(12) United States Patent
Castille (10) Patent No.: US 7,487,102 B2
(45) Date of Patent: Feb. 3, 2009

(54) PROCESS OF INTERFACING A PATIENT INDIRECTLY WITH THEIR OWN ELECTRONIC MEDICAL RECORDS

(76) Inventor: Debra Castille, 26005 E. 317 St., Harrisonville, MO (US) 64701

( * ) Notice: Subject to any disclaimer, the term of this patent is extended or adjusted under 35 U.S.C. 154(b) by 1074 days.

(21) Appl. No.: 09/802,546

(22) Filed: Mar. 9, 2001

(65) Prior Publication Data
US 2002/0128870 A1 Sep. 12, 2002

(51) Int. Cl.
*G06F 19/00* (2006.01)
*G06F 7/00* (2006.01)

(52) U.S. Cl. .......................................... 705/3; 707/102
(58) Field of Classification Search .................. 705/2, 705/3; 434/262, 358
See application file for complete search history.

(56) References Cited

U.S. PATENT DOCUMENTS

| 5,084,819 | A | * | 1/1992 | Dewey et al. | 434/262 |
|---|---|---|---|---|---|
| 5,435,324 | A | * | 7/1995 | Brill | 128/897 |
| 5,496,175 | A | * | 3/1996 | Oyama et al. | 434/118 |
| 5,644,778 | A | * | 7/1997 | Burks et al. | 705/2 |
| 5,664,109 | A | * | 9/1997 | Johnson et al. | 705/2 |
| 5,924,074 | A | * | 7/1999 | Evans | 705/3 |
| 6,151,581 | A | * | 11/2000 | Kraftson et al. | 705/3 |
| 2005/0187794 | A1 | * | 8/2005 | Kimak | 705/3 |

OTHER PUBLICATIONS

Jackson, William; "VHA rolls out patient record app in Alabama," Nov. 18, 1996 Government Computer News, v15, n29, p. 25(1).*

Edward H. Shortliffe, MD, PHD; The Evolution of Electronic Medical Records; pp. 1-16; 1999; Academic Medicine.
JA Gilbert; Physician data entry: providing options is essential; p. 1; Sep. 1998; Health Data Management.
McDonald, CJ, The Barriers to Electronic Medical Record Systems and How to Overcome Them, Journal of the American Medical Informatics Association, May-Jun. 1997.
Walsh, Stephen H., The clinician's perspective on electronic health records and how they can affect patient care, May 2004.
*Clinical Chemistry*; McDonald, Clement J., et al.; LOINC, a Universal Standard for Identifying Laboratory Observations: A 5-Year Update; 2003; 49:624-633.
*Clinical Chemistry*; Forrey, Arden W., et al.; Logical observation identifier names and codes (LOINC) database: a public use set of codes and names for electronic reporting of clinical laboratory test results; 1996; pp. 81-90.

* cited by examiner

*Primary Examiner*—C Luke Gilligan
*Assistant Examiner*—Rachel L Porter
(74) *Attorney, Agent, or Firm*—Hovey Williams LLP (57) ABSTRACT

A process of allowing a patient to have limited input access to their electronic medical record including the steps of forming a basic patient medical record in a computer through entry of information using a keyboard, providing the patient with a machine readable medical questionnaire concerning their history, environment, symptoms, and other pertinent information for answering by the patient, interfacing the machine readable medical questionnaire with a scanner to send the data stream to a microprocessor and converting the patient's answers to a protocol simulating the protocol from a party having authority to export data to the patient's medical record, and transferring the protocol-arranged data into the patient's medical record housed in a database through use of an interface engine.

15 Claims, 9 Drawing Sheets

PROCESS OF INTERFACING A PATIENT INDIRECTLY WITH THEIR OWN ELECTRONIC MEDICAL RECORDS

BACKGROUND OF THE INVENTION

1. Field of the Invention

This invention relates to the field of electronic transfer of patient-entered medical data to an existing electronic medical record. More particularly, it pertains to a unique process for transferring data into electronic medical records that relieve the doctor and his or her staff from the time-consuming job of data transfer under slower, prior art processes.

2. Description of the Prior Art

In the health care industry, certain governmental agencies have been created to deal with the problems facing doctors and medical insurance agencies such as the efficient transfer of patient medical data from one entity to another. One of these agencies, the Health Care Financing Administration, has established laws which increase the amount of data that must be captured for each patient visit. These laws require the doctor or nurse to ask certain questions and document the questions and responses in the patient's chart. The amount of time required to ask the appropriate questions and document the responses often consumes a large portion of the patient's office visit. There are over three hundred questions that can be asked of a patient to form a complete medical history (this includes the patient's past medical history, family history, social history, risk factors and symptoms.)

To help manage this continually increasing amount of medical data, many medical facilities invested millions of dollars in electronic medical records (EMR). An EMR is a computer application used to store patient-specific information. It contains all pertinent clinical information regarding a patient's health care. Though an EMR effectively manages the clinical data and provides a means for better patient care, the burden of data entry into the computer has discouraged acceptance of electronic medical records throughout the industry.

To help with this seemingly overload of medical data required for each patient, physicians began requesting a means to allow the patient to enter some of their own data into the computer. However, another law, the Health Insurance Portability and Accountability Act (HIPPA) prevents a patient from direct access to the EMR application because there is currently no secure method to prevent a patient from unauthorized access to other patients' charts.

Simultaneously, as more electronic systems were developed to manage medical information, standards were developed to govern the format for data exchange between disparate computer systems. These standards are generically labeled as "HL7", or Health Level 7, and govern the format for data exchange between scheduling, billing, medical records and laboratory systems. Software vendors usually specialize in only one of the medical systems and build interfaces to link to the other systems. Laboratory computers were then able to send laboratory data to an electronic medical record using the HL7 laboratory specifications. Scheduling systems were able to send scheduling information to the electronic medical records through the HL7 scheduling specifications.

Unfortunately, no system has been developed to send patient entered data into an electronic medical record. Unless the vendor of the EMR was willing to provide a module for patients, medical facilities had no way to allow patients to safely enter their own data. Though there had been numerous requests for such an application, EMR vendors had not responded to the public's need.

This invention is a product and a new process to satisfy this long-sought but as yet unsatisfied need for the data flow. The invention comprises the combination of the use of scanning technology and laboratory interface specifications to create a unique mechanism for the patient entered data to enter into an electronic medical record. The electronic medical record freely accepts the patient entered data because it believes it is coming from a laboratory system. This process had never been used before and made quite an impression when it was demonstrated at a national conference in April 2000.

The achievements of this invention are realized at eight levels: First, the invention satisfies a long-standing need of the medical community that has not been met before.

Second, the invention removes a barrier, helping to encourage the use of technology in the medical industry. The medical industry has recognized that using electronic medical records has drastically decreased errors, saving lives and promoting better patient care. It was discovered that an EMR not only helps to manage data, but can be very effective in eliminating common documentation errors thus saving millions of lives. Parenthetically, it has been found that medical documentation errors cause more deaths than a jumbo jet crashing every day. However, the increased time required to enter the data into the computer has discouraged some health care providers from moving to electronic media. This invention drastically decreases the clinician's data entry time because the patient has already been asked the questions and the answers have been transferred into the patient's electronic record before the nurse or physician enters the exam room. Physicians are more willing to use the electronic medical record now that the task of data entry has been decreased.

Third, the quality of the office visit is also improved. Because the physician starts with the answers, the time usually spent gathering and documenting the information can now be used focusing on the patient's problems and concerns.

Fourth, the invention aids in early detection of medical problems. This method has already proven effective in diagnosing medical problems that could otherwise have been hidden. Because the patient questionnaire is more extensive than most manual methods of gathering data, the physician is given a more comprehensive view of the patient's condition. With this information, the physician is alerted to question the patient in more detail concerning conditions that have been revealed through use of the questionnaires.

Fifth, the invention helps the patient get what they want from an office visit. The patient is able to participate more in their own medical care. This method allows patients an opportunity to spend more time considering and documenting their medical condition. Patients often feel rushed while in an exam room and forget to mention a concern to the physician. After returning home, they call to speak to a nurse who then must question the physician and return a call to the patient. This method serves as a reminder to the patient concerning symptoms and conditions that they may otherwise have forgotten to tell the physician.

Sixth, the invention aids in meeting legal requirements. Laws governing medical documentation have increased, causing financial hardships on many medical practices. When documentation requirements are not met, clinics are fined and can suffer considerable financial loss. This invention not only transfers the data into the EMR, but also can insert the data as part of the current office visit documentation. Using this invention, a clinic is able to meet the increased documentation requirements.

Seventh, the invention provides a secure path for patient interaction with their record. Laws governing the privacy of a patient's medical record have been a challenge to medical organizations that see a need for patient interaction with their record but have not been able to find a safe method to allow that interaction. This invention provides a safe, easy to use and effective means for the patient's communication to enter into the their record without compromising security.

Finally, the invention aids in medical research. Gathering accurate data for research to improve patient care has been a long-standing problem. The invention provides a mechanism to capture complete data and write it in a consistent format, easing the burden of research. Because many facilities throughout the country will be using the same questionnaires, valuable data can be retrieved nationwide to aid in research to improve patient care.

SUMMARY OF THE INVENTION

The first step in the process of this invention is to provide a patient with a questionnaire in the form of a "bubble" scan card (a paper based form with questions and designated areas for patient responses) when arriving at the medical facility. They are also given a pencil and asked to mark the "bubbles" for their answers. The cards can also be mailed to the patient and returned via mail back to the clinic.

The card is then given to the receptionist (or whomever is designated to run the process. The receptionist receives the completed card from the patient. Using a computer and keyboard, the receptionist types the patient identification information, such as first name, last name, date of birth, social security, sex, etc. into the computer application supplied with the invention. The receptionist then places the scan card into the scanner. The scanner reads the data from the card and sends a stream of data through a cable attached to a serial port on a computer used in the doctor's office. The data stream is then read and evaluated by the software accompanying the invention. The data is then converted into an HL7 message containing the patient responses and is written to a location specified by the doctor's office during the initial install of the invention. The patient's data, now an HL7 record, may be picked up by an interface engine (not part of the invention) and written to the patient's chart. Because the invention uses HL7 laboratory standards, any HL7 compliant application is able to easily use this process. The next step is for the doctor or his or her staff to access the patient's electronic record, having the questions and answers displayed for their review. They can now start with the patient's answers, making the office visit much more beneficial to the patient, and making the use of an electronic medical record more acceptable by the physician.

Accordingly, the main object of this invention is a process that satisfies a long-standing need of the medical community that has not been met before. Other objects of the invention include the removal of a barrier, helping to encourage the use of technology in the medical industry; a process that drastically decreases the clinician's data entry time because the patient has already been asked the questions and the answers have been transferred into the patient's electronic record before the nurse or physician enters the exam room; a process that improves the quality of the office visit; a process that helps the patient get what they want from an office visit by being able to participate more in their own medical care; a process that aids in meeting legal requirements; a process that provides a secure path for patient interaction with their record; a process that provides a safe, easy to use and effective means for the patient's communication to enter into the their record without compromising security; and, a process that aids in medical research.

These and other objects of the invention will become more clear when one reads the following specification, taken together with the drawings that are attached hereto. The scope of protection sought by the inventor may be gleaned from a fair reading of the Claims that conclude this specification.

PREFERRED EMBODIMENTS

Turning now to the drawings where figures and elements are identified by numbers and described below with like numbers and elements, a complete explanation of the process is described.

Figure 1:
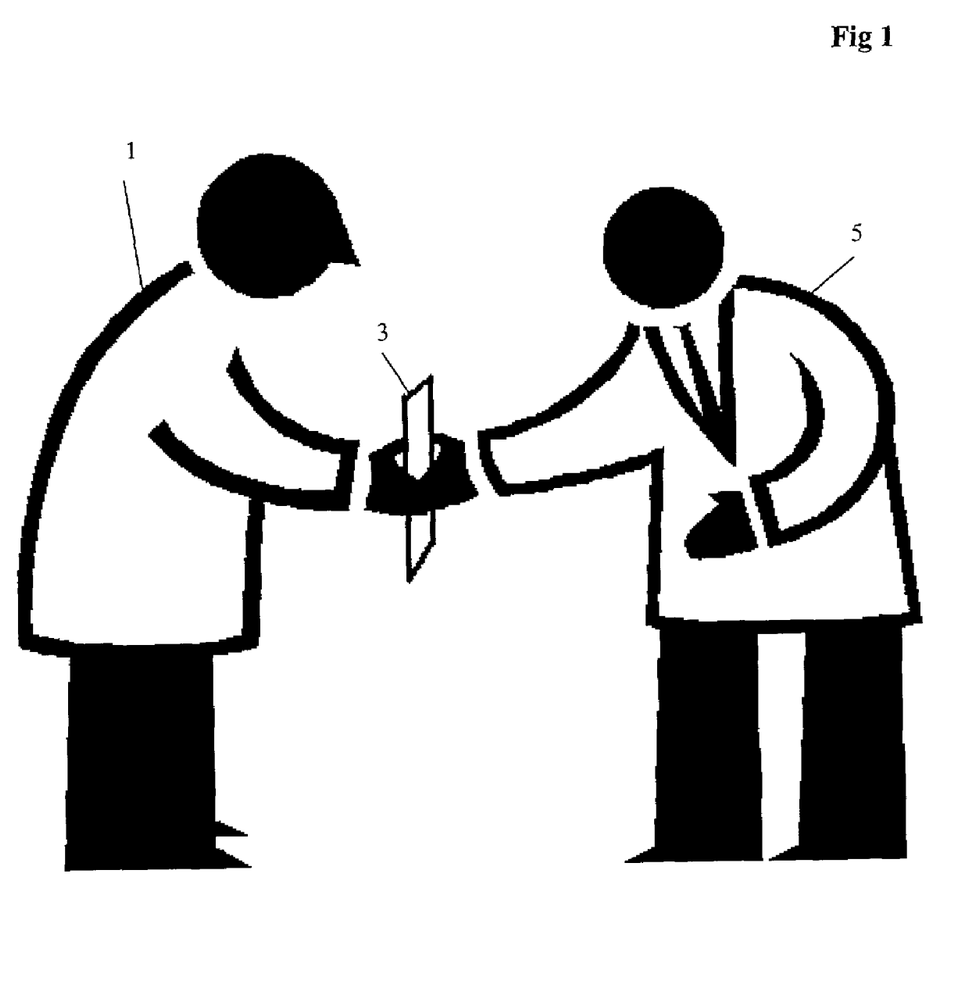
FIG. 1 shows a patient (1) accepting a questionnaire from a member (3) of the doctor's staff (5).

FIG. 1 shows a patient (1) accepting a questionnaire (3) from a member of the doctor's staff (5). The questionnaire may be given to the patient within a clinic setting or mailed to the patient prior to an office visit.

Figure 2:
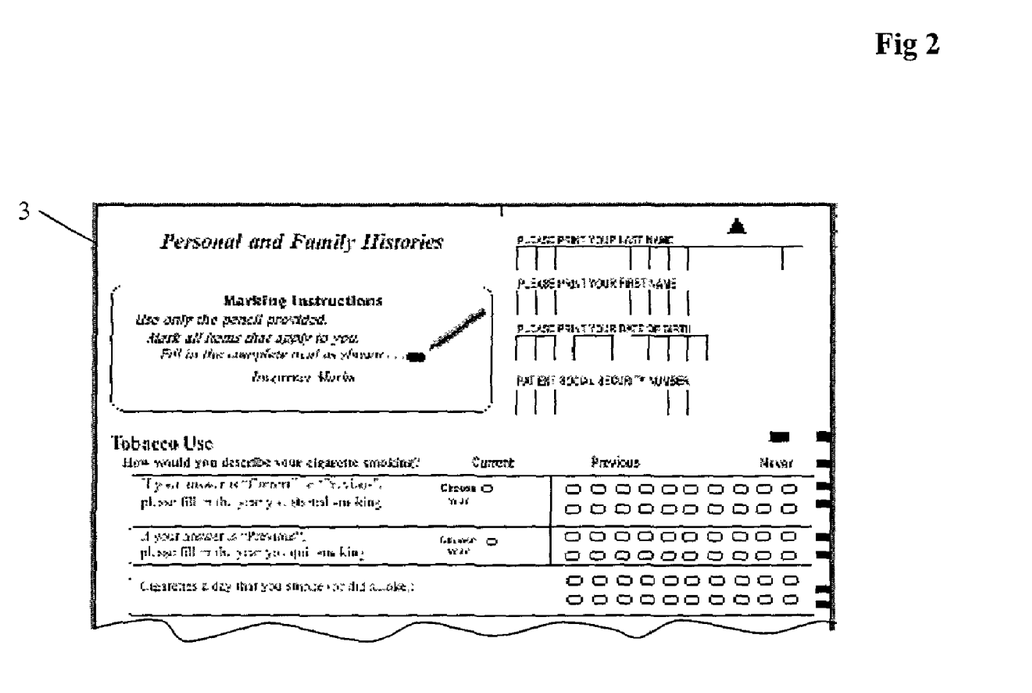
FIG. 2 shows a typical machine readable questionnaire (3).

FIG. 2 shows a typical machine readable questionnaire (3). The questionnaire requires patient identification information (name, date of birth, social security number) to be written on the card to aid in uniquely identifying the patient within the electronic medical record. The card consists of a series of questions with applicable answers for the patient to consider. The card may contain multiple choice answers or open boxes for patient responses. An example of a machine readable card is the Review of Systems card designed by the inventor and printed by Lincolnshire Printing at 436 Morris Street, Mundelein, Ill.

Figure 3:
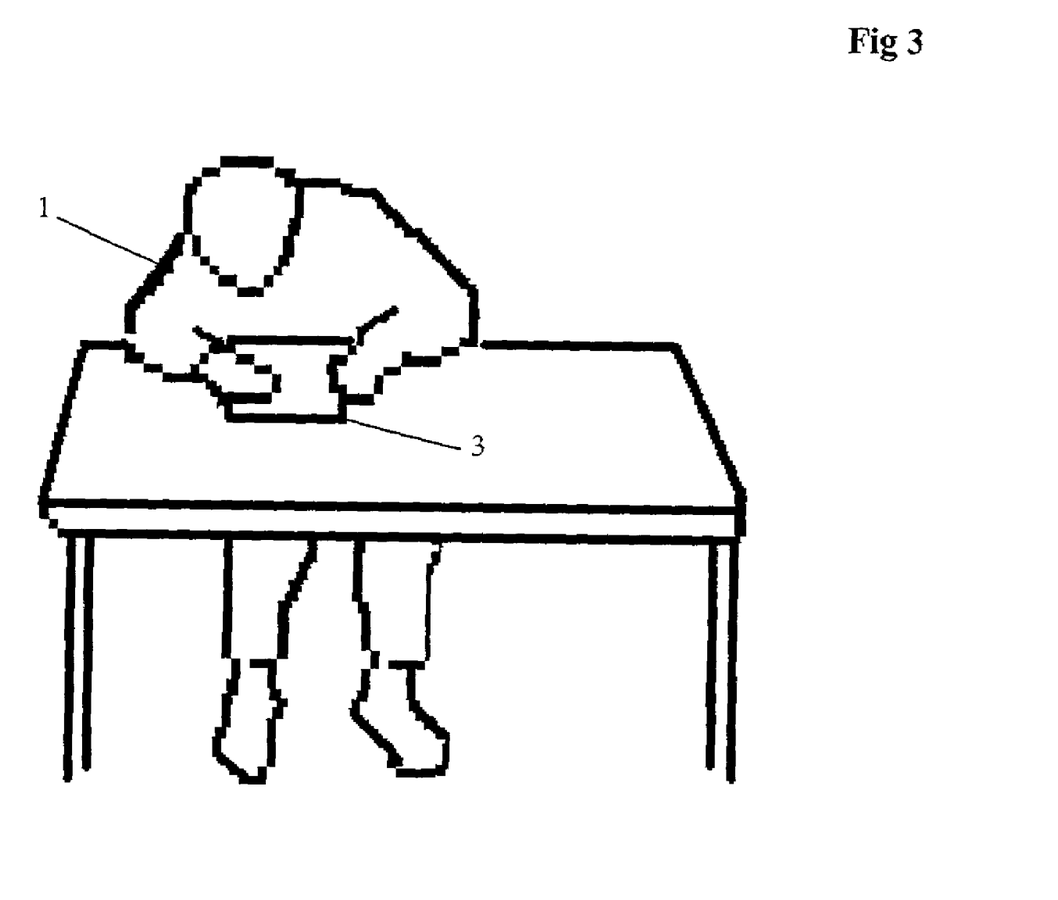
FIG. 3 shows a patient (1) completing a questionnaire (3).

FIG. 3 shows a patient (1) completing a questionnaire (3). The patient uses a pencil or pen to mark the answers onto the card. This illustration depicts a patient in a medical office setting, but may also apply to an alternate method whereupon the patient receives the questionnaire through a mail service.

Figure 4:
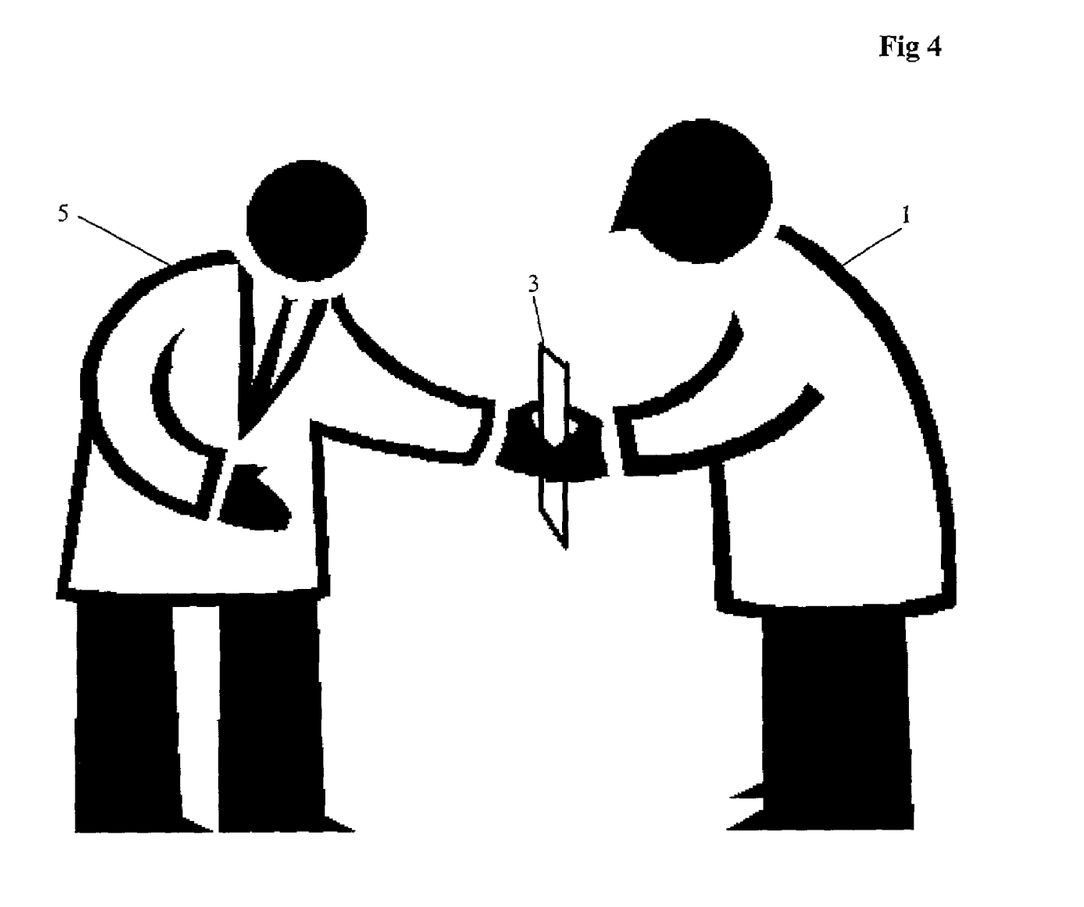
FIG. 4 shows a patient (1) returning the questionnaire (3) to the doctor's staff (5).

FIG. 4 shows a patient (1) returning the questionnaire (3) to the doctor's staff (5). This illustration depicts a flow in which the patient is returning to the doctor's office for an appointment. An alternate flow would allow a patient to return the questionnaire through a mail service. This would allow a clinic to monitor a patient's status without the patient having to return for a visit to the physician's office. (This is an effective method for elderly patients who have difficulty with mobility as well as for patients participating in research studies where questionnaires can easily facilitate the necessary data capture.)

Figure 5:
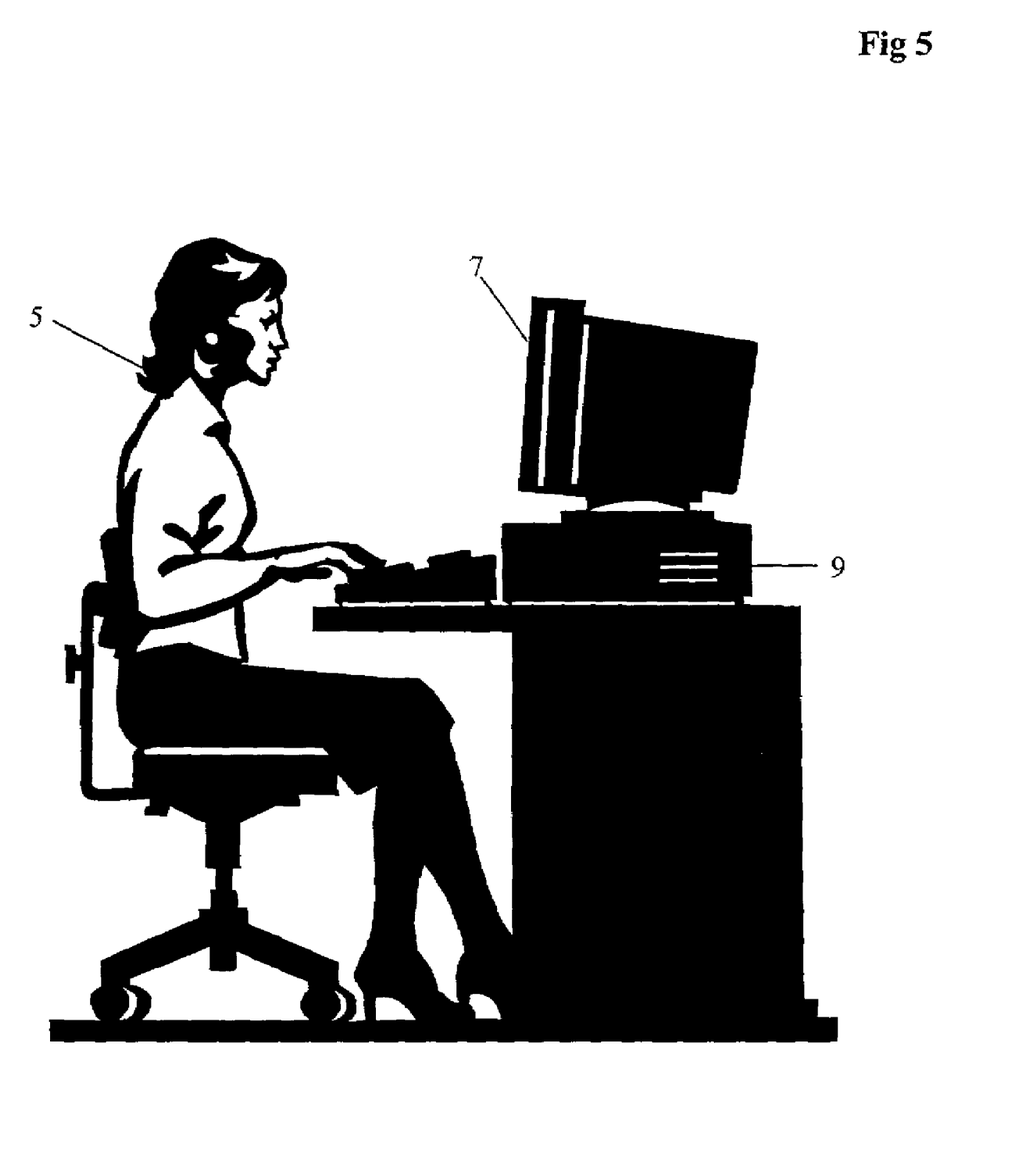
FIG. 5 shows a member of the doctor's staff (5) entering patient identification information (name, date of birth, social security number) into the computer application (7) supplied with the invention and loaded onto the computer (9).

FIG. 5 shows a member of the doctor's staff (5) entering patient identification information (name, date of birth, social security number) into the computer application (7) supplied with the invention. This process allows the staff personnel to uniquely identify the patient within the electronic medical record to assure that the data is sent to the correct patient chart within the EMR. An example of a computer (9) useful herein is a Compaq Presario 5151 with a Window's operating system. This figure shows the computer application in use by the front desk staff at the reception desk, but an alternative workflow would allow a nurse or medical technician to start the process in the clinic after bringing the patient to the exam room.

Figure 6:
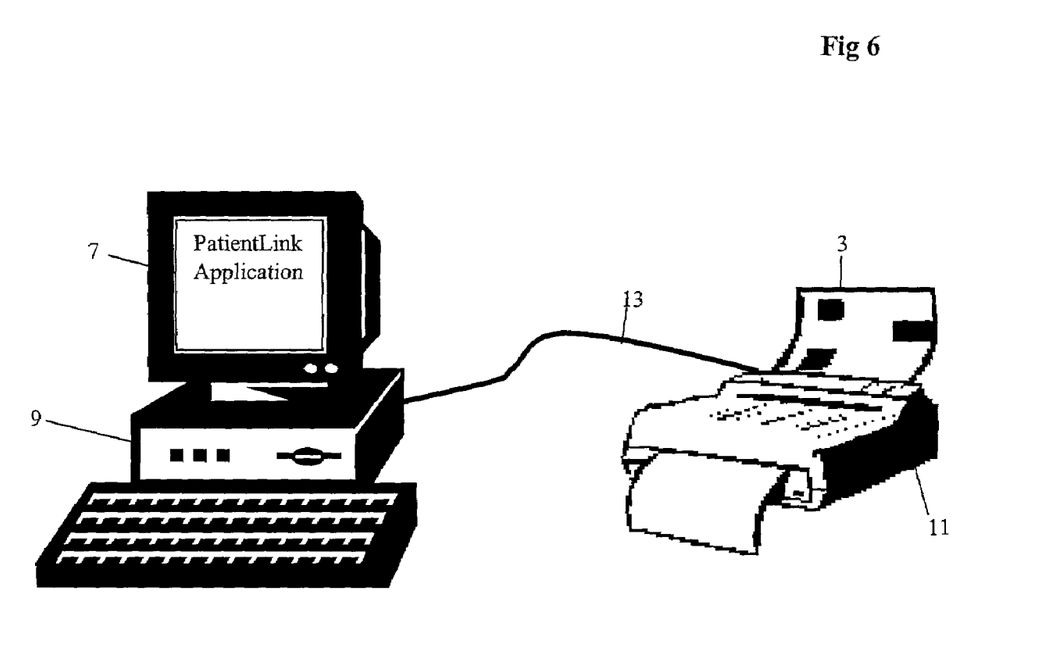
FIG. 6 shows a machine readable questionnaire (3) being read by a scanner (11) which is attached to a computer (9), via a cable (13), containing the invention application (7).

FIG. 6 shows a machine readable questionnaire (3) being read by a scanner (11). The scanner must be attached to the computer (9) containing the computer application (7) supplied with the invention. The questionnaire is scanned and the data from the questionnaire is sent from the scanner (11) into the computer (9) via a cable (serial cable or ups cable) (13) and then read by the application (7) supplied with the invention. An example of a scanner is the Chatsworth 9002 scanner made by Chatsworth Data at 20710 Lassen Street, Chatsworth, Calif.

Figure 7:
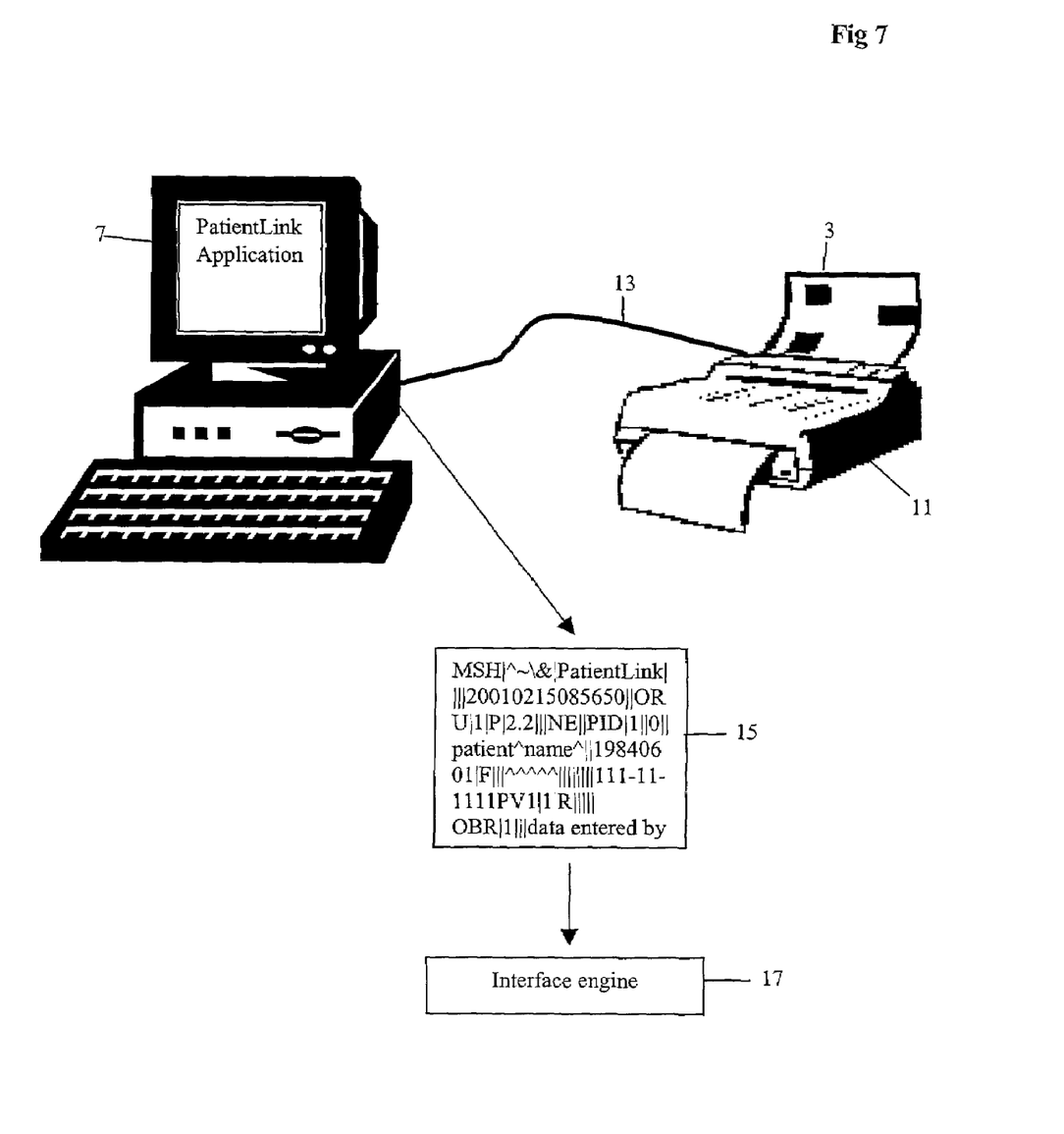
FIG. 7 shows the scan card (3) being read by the scanner (11) and sending the data, via a cable (13), to the computer application (7) supplied with the invention. The data is formatted into the accepted protocol (15) for sending to the interface engine (17).

FIG. 7 shows the scanner (11) reading the scan card (3) and sending the data stream via a cable (13) to the computer application (7) supplied with the invention. The application converts the data stream into an HL7 laboratory record (15) to make it acceptable to the electronic medical record interface engine (17). It will be appreciated that the present invention is not limited to the use of HL7, and those skilled in the art will recognize that other communications protocols, such as a protocol created by the American Society for Testing and Materials (ASTM), may be used in a manner substantially similar to HL7 as described herein. The HL7 record contains the patient's answers to the questionnaire and the database element names identifying where the answers should be written within the EMR database.

Figure 8:
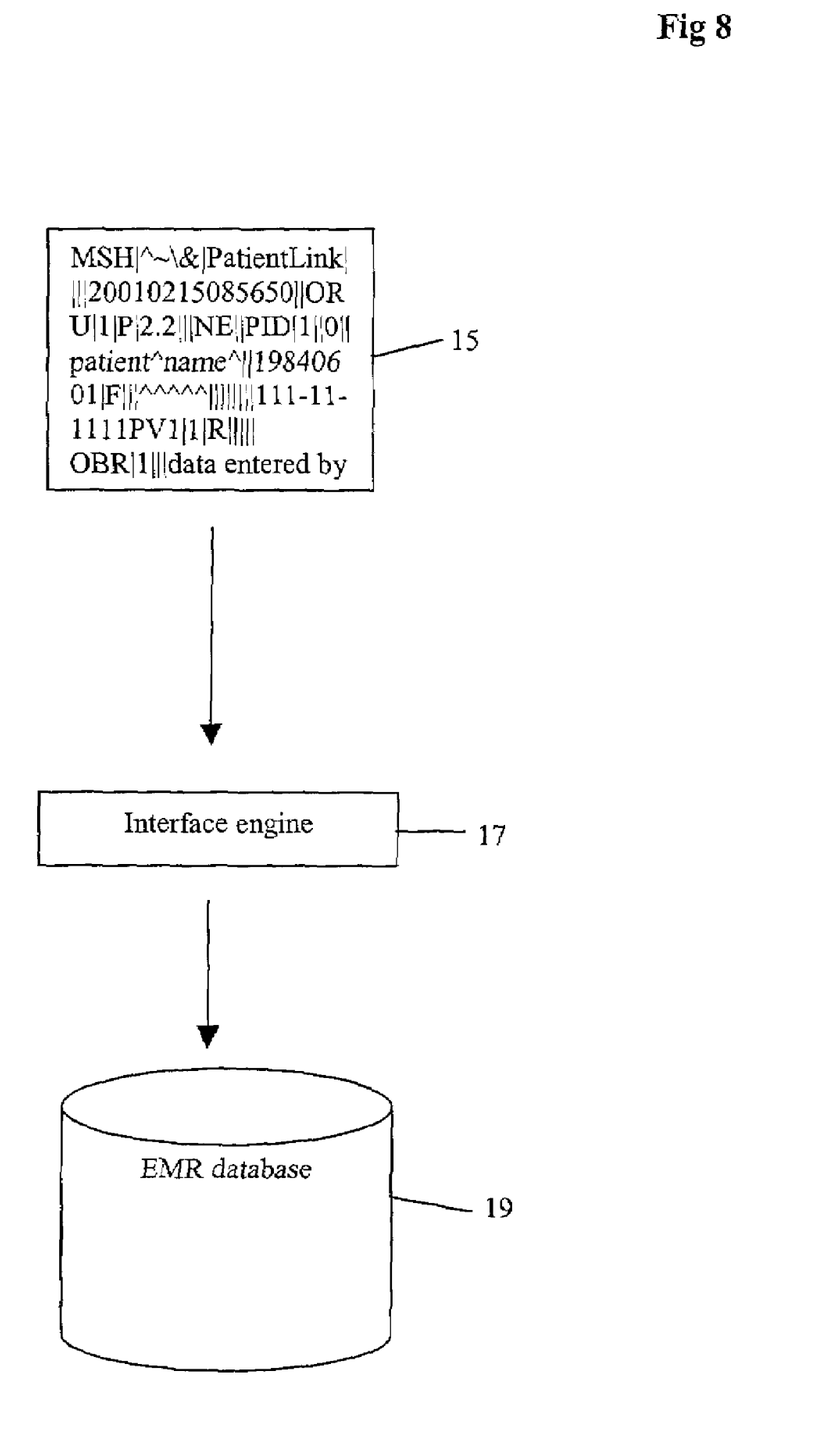
FIG. 8 shows the HL7 laboratory record (15) being accepted by the EMR interface engine (17) and being sent into the EMR database (19).

FIG. 8 shows the HL7 laboratory record (15) being accepted by the EMR interface engine (17). Because the record is defined as a laboratory record, the computer interface accepts the file as coming from a valid data portal. The data enters through the interface and is written to the EMR database (19).

Figure 9:
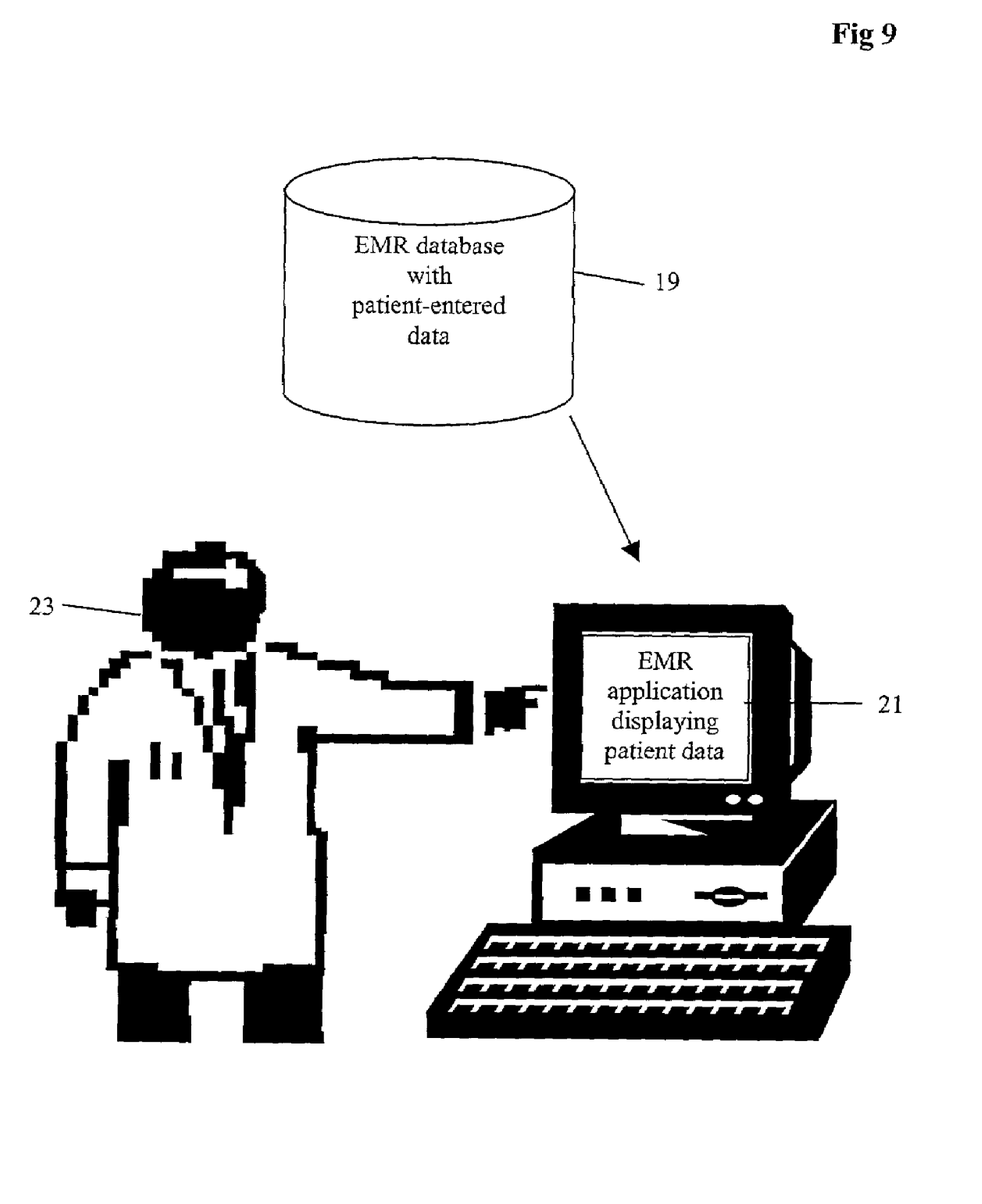
FIG. 9 shows the data residing in the EMR database (19) and displayed in the EMR application (21) for review by the nurse and/or physician (23).

FIG. 9 shows the data residing in the EMR database (19) and displayed within the EMR application (21) for review by the nurse and/or physician (23). The questions from the questionnaire and the answers supplied by the patient are displayed as a comprehensive view of the patient's current health status. The physician is now able to use his/her time to focus on the patient's symptoms and concerns as documented in the EMR chart. The physician is free to interact with the EMR to input additional information upon further questioning of the patient.

What is claimed is:

1. A process of allowing a patient to have limited input access to their electronic medical record, the method comprising the steps of:

a) providing the patient with a machine readable card including a questionnaire concerning the patient's medical history, environment, symptoms, or other pertinent information for answering by the patient;

b) receiving the patient's medical history, environment, symptoms, or other pertinent information from the patient in response to the questionnaire provided on the machine readable card;

c) interfacing the machine readable card with a scanning type machine to convert the patient's written answers to a data stream;

d) arranging the data stream into a defined data structure simulating the protocol structure from a party having authorization to export data to the patient's patient-specific electronic medical record;

e) sending the arranged data stream to an assigned location for importing into a patient's patient-specific electronic medical record, wherein the patient's electronic medical record contains patient-specific, clinical information regarding the patient's health;

f) verifying that the arranged data stream is authorized to be imported into the patient's electronic medical record; and (g) importing into the patient's electronic medical record the verified data, including patient's medical history, environment, symptoms, or other pertinent information provided by the patient on the machine readable card.

2. The process of claim 1, further comprising the step of forming a basic patient medical record in a computer through entry of information using a keyboard by a professional staff member.

3. The process of claim 1, wherein the machine readable questionnaire includes questions concerning the systems making up the human body with designated locations for patient responses.

4. The process of claim 1, wherein the step of interfacing the machine readable card with the scanning type machine is accomplished by a member of the clinical staff 5. The process of claim 1, further comprising the step of converting and arranging the data stream to a defined set of data structures simulating the protocol of Health Level Seven (HL7).

6. The process of claim 1, further comprising the step of arranging the data stream into a defined data structure according to a protocol of ASTM (American Society for Testing and Materials).

7. The process of claim 1, further comprising the step of receiving the formatted data with an interface engine and sending it to a database containing the patient's electronic medical record.

8. The process of claim 2, wherein the computer is a standard PC microcomputer and the keyboard is compatible with the computer.

9. The process of claim 3, wherein the machine readable card is a paper answer sheet comprised of questions with designated areas for patient responses.

10. The process of claim 7, wherein said database is any database that accepts HL7 or ASTM messaging.

11. The process of claim 5, wherein the step of arranging the data stream into a defined set of data structures simulating the protocol from a party having authorization to export data into the patient's electronic medical record includes the step of accepting the data stream from the scanning type machine and arranging the data stream into a defined set of data structures simulating the HL7 specification.

12. A method of supplementing a medical record with information submitted by a patient, the method comprising the steps of:

providing the patient with a machine readable form including a questionnaire concerning the patient's medical history, environment, symptoms, or other pertinent information for answering by the patient;

receiving from the patient the machine readable form including the questionnaire at least partially completed so as to provide the patient's medical history, environment, symptoms, or other pertinent information converting the information on the machine readable form to machine-processable data;

communicating the data to a computer;

arranging the data into a defined data structure simulating the protocol structure from a party having authorization to export data to the patient's patient-specific electronic medical record;

communicating the arranged data to an electronic medical record interface;

verifying that the arranged data is authorized to be added to the patient's electronic medical record; and adding the verified data to the patient's electronic medical record, wherein the patient's electronic medical record contains patient-specific, clinical information regarding the patient's health.

13. The method as set forth in claim 12, further comprising the steps of:

mailing the form to the patient prior to the appointment; and presenting the patient's electronic medical record to the physician, including the information from the form, before the patient visits the doctor to apprise the physician of the patient's health status in the patient's absence.

14. A method of supplementing a medical record with information submitted by a patient, the method comprising the steps of:

providing the patient with a machine readable form including a questionnaire concerning, the information to be submitted by the patient, the patient's medical history, environment, and symptoms;

receiving from the patient, prior to a visit with a physician, the machine readable form filled out by the patient and providing the information submitted by the patient in response to the questionnaire;

converting the information on the form to machine-processable data;

communicating the data to a computer;

arranging the data into a defined data structure simulating a Health Level Seven laboratory record, wherein the laboratory record includes the information from the form and information identifying an electronic medical record that is personal to the patient;

communicating the arranged data to an electronic medical record interface; verifying that the arranged data is authorized to be added to the patient's electronic medical record; and adding the verified data to the patient's electronic medical record, wherein the patient's personal electronic medical record contains patient-specific, clinical information regarding the patient's health.

15. The method as set forth in claim 13, further comprising the steps of:

mailing the form to the patient prior to the appointment; and presenting the patient's electronic medical record to the physician, including the information from the printed form, prior to the visit to inform the physician of the patient's health status.

* * * * *